(12) United States Patent
Brons et al.

(10) Patent No.: US 7,949,092 B2
(45) Date of Patent: May 24, 2011

(54) DEVICE AND METHOD FOR PERFORMING X-RAY ANALYSIS

(75) Inventors: Gustaaf Christian Simon Brons, Ootmarsum (NL); Petronella Emerentiana Hegeman, Borne (NL)

(73) Assignee: Panalytical B.V., Almelo (NL)

( * ) Notice: Subject to any disclaimer, the term of this patent is extended or adjusted under 35 U.S.C. 154(b) by 608 days.

(21) Appl. No.: 12/110,035

(22) Filed: Apr. 25, 2008

(65) Prior Publication Data
US 2011/0058648 A1 Mar. 10, 2011

Related U.S. Application Data

(62) Division of application No. 11/501,309, filed on Aug. 8, 2006, now abandoned.

(51) Int. Cl.
*G01N 23/223* (2006.01)

(52) U.S. Cl. .......................................... 378/44; 378/45
(58) Field of Classification Search ............... 378/44–50
See application file for complete search history.

(56) References Cited

U.S. PATENT DOCUMENTS

| | | | |
|---|---|---|---|
| 5,778,039 A * | 7/1998 | Hossain et al. | 378/45 |
| 6,381,303 B1 * | 4/2002 | Vu et al. | 378/46 |
| 2008/0159475 A1 * | 7/2008 | Mazor et al. | 378/50 |

* cited by examiner

*Primary Examiner* — Hoon Song
(74) *Attorney, Agent, or Firm* — Robert A Jensen; Jensen & Puntigam, P.S.

(57) ABSTRACT

The invention relates to a device for performing X-ray analysis. Device 1 comprises an X-ray tube 2 and at least one capillary lens 4 for focusing the X-rays in a micro-region at a location 5 for a sample for analysis. Device 1 further comprises a detector 6 for detecting X-ray fluorescence from the sample. Device 1 further comprises at least one energy-dependent filter 3 placed between the X-ray tube 2 and the capillary lens 4. The filter 3 is adapted to substantially block X-rays with an energy which is lower than a predetermined threshold value.

7 Claims, 2 Drawing Sheets

DEVICE AND METHOD FOR PERFORMING X-RAY ANALYSIS

This is a divisional application of U.S. patent application Ser. No. 11/501,309 filed Aug. 8, 2006.

The invention relates to a device for performing X-ray analysis, more particularly analysis of X-ray fluorescence originating from a relatively small irradiated region of a sample.

X-ray fluorescence (XRF) spectrometry is generally applied for the purpose of identifying and determining concentrations of elements in specimens of materials, be it in solid, liquid or powder form.

There is a wish in different technical fields to irradiate only a relatively small region (micro-region) of a sample for analysis. The desired dimensions of the micro-region to be irradiated lie, as an indication, in the order of magnitude of several tens of to several thousand square micrometers. Particularly in the semiconductor industry, where semi-manufactures are usually analyzed, surrounding electronics in this way remain practically non-irradiated, and the risk of possible damage due to the effect of X-rays can be avoided.

The invention has for its object to provide a device of the type stated in the preamble which fulfils this wish.

The device according to the invention comprises for this purpose an X-ray tube and at least one capillary lens for focusing the X-rays in a micro-region at a location for a sample for analysis, in addition to a detector for detecting X-ray fluorescence from the sample, wherein the device further comprises at least one energy-dependent filter placed in the optical path between the X-ray tube and the sample location, wherein the filter is adapted to block in considerable measure X-rays with an energy which is equal to or lower than a predetermined energy value, this such that the dimensions of the micro-region are substantially bounded within predetermined permissible values.

The X-ray tube and the capillary lens together generate an X-ray beam in a micro-region at the sample location. The invention is based on the insight that the dimensions of the irradiated region at the sample location are energy-dependent: at lower energies the irradiated region is larger. The dimensions of the irradiated region can be bounded within predetermined permissible values by applying an energy-dependent filter placed in the optical path between the X-ray tube and the sample location. The setting of the threshold value of the filter determines the realized dimensions of the irradiated region. The device according to the invention has the further advantage that diffraction peaks occurring at an energy which is equal to or lower than the predetermined energy value of the filter are eliminated. This implies a significant improvement in the reliability of the outcome of the X-ray analysis.

In a first preferred embodiment the filter comprises aluminium. The thickness of the filter is preferably smaller than or equal to 300 micrometers. The thickness of the filter must provide an optimum between the desired transmission characteristics of the filter and the intensity per energy value required at the position of the sample location.

In a further preferred embodiment the X-ray tube is adapted to generate an X-ray beam with a microfocus. Suitable low-power microfocus tubes are obtainable in the field.

In a practical preferred embodiment the filter is placed in the optical path between the X-ray tube and the capillary lens.

According to yet another preferred embodiment, the capillary lens is a polycapillary lens. A polycapillary lens is highly suitable for focusing the filtered X-ray beam of the microfocus tube on the sample location.

The invention also relates to a method for performing X-ray analysis using a device according to the invention, comprising the steps of:
a) determining the desired maximum dimensions for the micro-region;
b) determining the energy of the X-rays associated with the desired maximum dimensions for the micro-region;
c) selecting a filter which is adapted to block in considerable measure X-rays with an energy which is equal to or lower than a predetermined energy value, wherein the energy value is chosen to be substantially equal to the energy determined in step b).

Using the method according to the invention a suitable filter can be selected for any application.

According to a preferred embodiment, step c) of the method comprises the following steps of:
1) selecting filter material that is suitable for blocking in considerable measure X-rays with an energy which is equal to or lower than the energy determined in step b);
2) determining the transmission characteristic in a number of filters with differing thickness of the selected filter material; and
3) selecting a thickness for the filter material associated with a predetermined value for the permissible transmission of X-rays with an energy equal to the energy determined in step b).

The invention will be described further on the basis of the drawings, in which:

FIG. 1 shows schematically the most important components of device 1 according to the invention in their mutual interrelation. Device 1 is generally intended for analysis of materials using XRF spectrometry.

Figure 1:
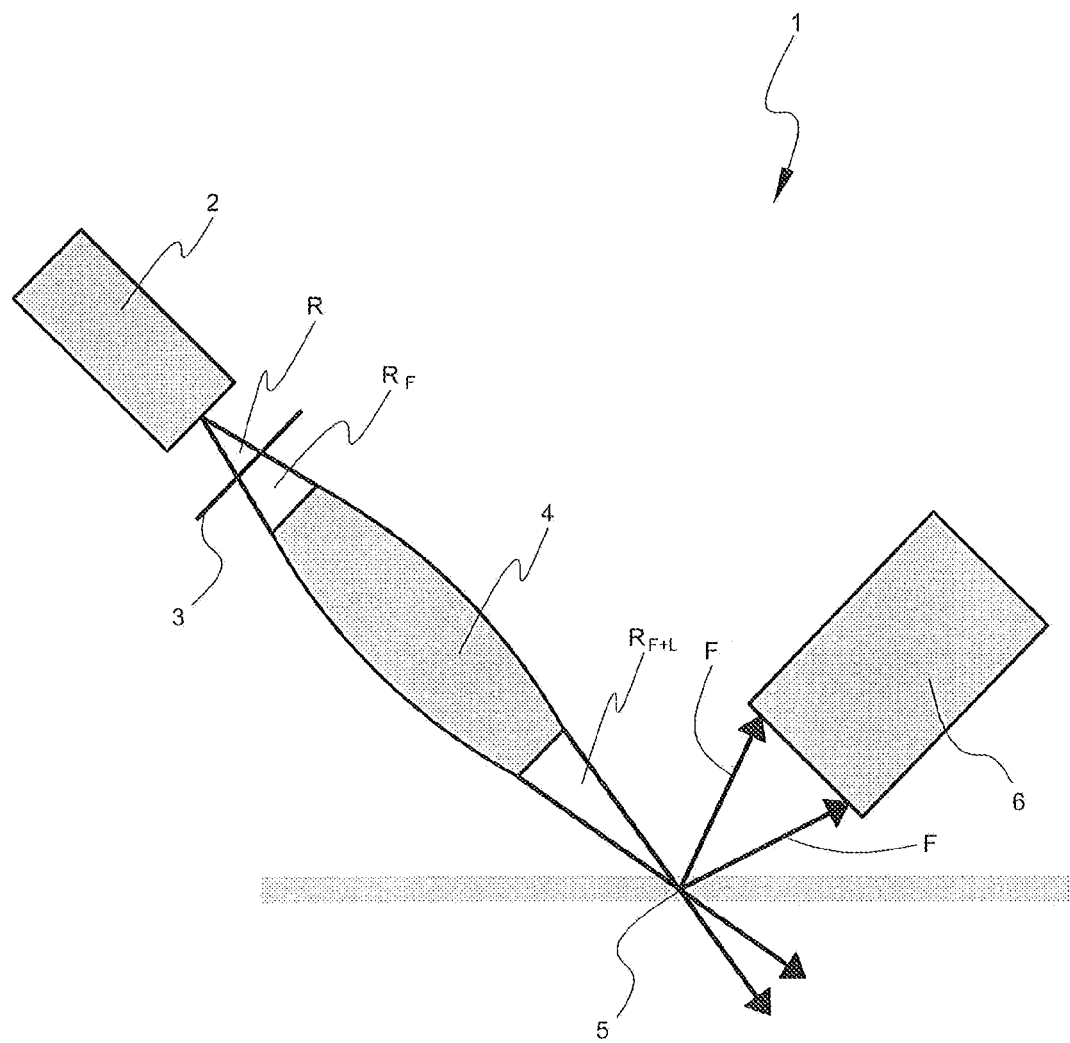
FIG. 1 shows a diagram of a preferred embodiment of the device according to the invention.

Device 1 comprises an X-ray tube 2, an energy-dependent filter 3, a capillary lens 4, a sample location 5 and an X-ray detector 6.

X-ray tube 2 is preferably adapted to generate an X-ray beam R from a microfocus. In the context of this invention a microfocus is understood to mean a focus on the anode with dimensions in the order of several tens to about 100 micrometers (L+W)/2, this also being referred to in the technical field as "focal spot size". Such an X-ray tube is commercially available and is referred to in the field as a microfocus tube. An example of a suitable microfocus tube is "Series 5000 Packaged X-ray tubes", marketed by Oxford Instruments, X-ray Technology established in Scotts Valley Calif., United States of America.

Filter 3 is placed in the optical path between X-ray tube 2 and capillary lens 4. Filter 3 is adapted to block in considerable measure X-rays from beam R with an energy which is equal to or lower than a predetermined energy value. The predetermined energy value depends on the desired dimensions for setting the region to be irradiated, this being illustrated on the basis of FIGS. 2A and 2B. Material with a K-absorption edge which is less than or equal to 2 keV results in a smooth transmission curve for the filter. Different materials meet this requirement, including aluminium, silicon, carbon. The thickness of the filter lies in the range up to 300 micrometers, preferably in the range of 50 to 200 micrometers. The thickness of the filter must be chosen as optimum between the desired transmission characteristics on the one hand and the energy efficiency of the X-ray tube on the other. The X-ray beam passing through filter 3 is designated $R_F$.

Figure 2A:
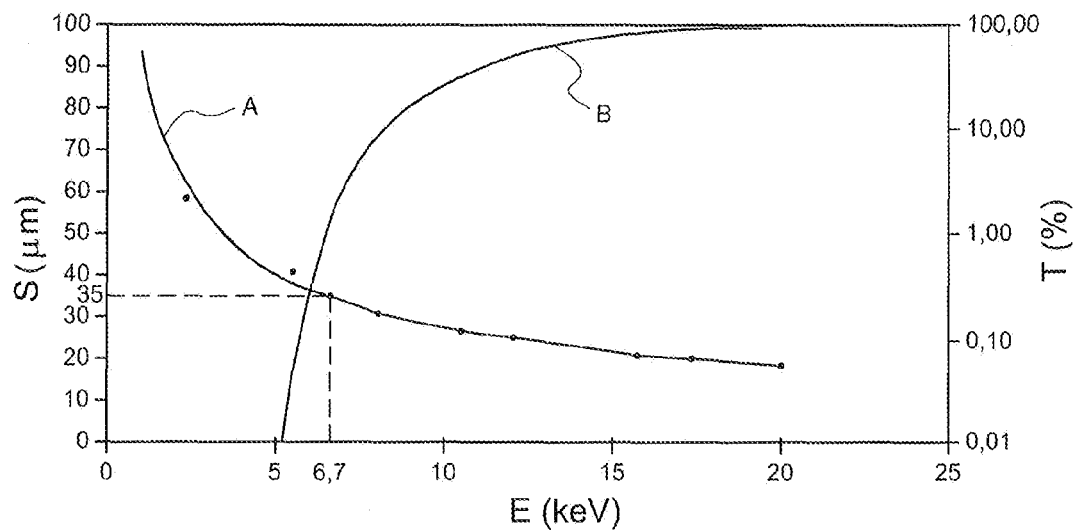
FIG. 2A shows in a graph the relation between the spot size (curve A) and the transmission of a filter suitable for the invention (curve B) plotted against the energy of the X-rays.

FIG. 2A shows two curves in one graph: curve A illustrates the spot size S of the X-rays at different energies and curve B shows the transmission characteristic T of a filter suitable for the invention. For the purpose of curve A the spot size associated with the irradiated region, or micro-region, on the sample is plotted on the left on the vertical axis and expressed in micrometer Full Width Half Max (FWHM). The energy of the X-rays expressed in kilo-electron volts is shown on the horizontal axis. Curve A clearly shows the trend that the spot size decreases as the energies increase. For the purpose of curve B the percentage transmission of the filter is shown on the vertical axis.

The graphs show measurements on device 1 according to the invention in the described preferred embodiment. Filter 3 is here an aluminium filter with a thickness of 200 micrometers.

Figure 2B:
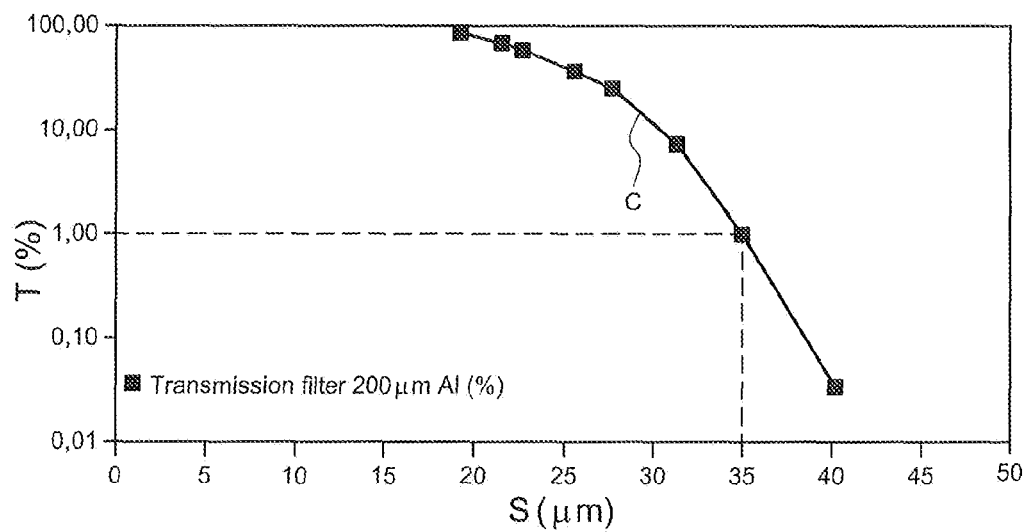
FIG. 2B illustrates in a graph the relation between the transmission and the spot size.

FIG. 2B shows a graph with curve C therein which illustrates schematically the resulting spot size of microfocus tube 2 on a sample 5 for analysis after applying the filter 3 as described with reference to FIG. 2A. The horizontal axis shows the dimensions of spot size S on the sample expressed in micrometer Full Width Half Max (FWHM). The vertical axis shows the percentage transmission T of filter 3.

From curve C can clearly be seen the trend that a minimization of the spot size can be achieved in a device according to the invention. In the preferred embodiment of device 1 can be seen that filter 3 transmits the most X-rays at a spot size of between approximately 20 and 25 FWHM.

By means of the method according to the invention a suitable filter can be selected for a device according to the invention for any intended application.

The method steps are described and elucidated below by means of a numerical example.

In a first step in the desired maximum dimensions $S_{max}$ for the micro-region are determined. In the context of the numerical example the spot size $S_{max}$ is determined at 35 micrometer FWHM.

In a second step the energy $E_{max}$ of the X-rays associated with the desired maximum dimensions $S_{max}$ for the micro-region is determined. This $E_{max}$ can be directly derived from curve A which shows the relation between these two quantities. In the chosen numerical example $E_{max}$ has the value 6.7 keV.

In a third step a filter is selected which is adapted to block in considerable measure X-rays with an energy which is equal to or lower than $E_{max}$, in this numerical example 6.7 keV.

The selection of a suitable filter is carried out according to the invention on the basis of the following steps.

A choice must first be made for a filter material that is suitable for blocking in considerable measure X-rays with an energy which is equal to or lower than $E_{max}$, in this numerical example 6.7 keV. In this example a choice has been made for aluminium.

The transmission characteristic is subsequently determined for one or more filters of differing thickness of the selected filter material. In this example curve B is determined for an aluminium filter of a thickness of 200 micrometers.

In order to select a suitable thickness for the filter, the permissible transmission for X-rays with an energy $E_{max}$ has to be determined. In this numerical example the permissible transmission for 6.7 keV is approximately 1%. The aluminium filter of 200 micrometer thickness is found to readily satisfy this criterion.

It is noted for the sake of completeness that the relation between spot size S and energy E also depends on the capillary 4. Curves A and C must therefore be determined separately for each configuration of device 1.

Capillary lens 4 focuses the beam $R_F$ as a beam $R_{F+L}$ on the sample location 5. Lens 4 can be both a polycapillary and a monocapillary lens. Diverse suitable capillary lenses are commercially available.

During operation device 1 irradiates a relatively small region (micro-region) of a sample at sample location 5. The dimensions of the irradiated micro-region can be derived directly from dimensions of the spot size in micrometer FWHM. The following relation known in the field can be used for this purpose:

$$FWHM/2.36 = sigma$$

wherein 6*sigma shows the so-called footprint, i.e. the dimensions of the region on the sample within which 99.7% of the X-radiation is incident.

The spot size between approximately 20 and 25 FWHM results in a footprint of between 50 and 60 micrometers respectively. Dimensions of the irradiated region, or micro-region, in the order of magnitude of 50×50 micrometers are therefore feasible with the embodiment described herein. This makes device 1 particularly suitable for analysis of the composition of so-called wafers in the semiconductor industry.

The device according to the invention has the further important advantage that the diffraction peaks, which occur at energy values falling within the energy range largely blocked by the filter, are generally eliminated. In the shown and described preferred embodiment of device 1 the diffraction peak occurring in a sample Si(100), which is normally visible at 5.5 keV, is for instance eliminated.

Detector 6 is adapted to detect X-ray fluorescence F coming from the irradiated region in the sample. Diverse suitable X-ray detectors are commercially available.

It is noted that device 1 is described in the context of Energy Dispersive (ED) XRF. It will however be apparent to a skilled person in the field that the invention is not limited thereto, but is also very readily applicable in the case of Wavelength Dispersive (WD) XRF. In FIG. 1 an analyzer crystal (not shown) must then for instance be placed in the optical path between sample location 5 and detector 6.

Finally, the invention is expressly not limited to the described and shown embodiment. In addition to the described combination of a microfocus tube with a polycapillary lens, the combination of a standard X-ray tube with a capillary lens can particularly also be envisaged, even though this is energetically less efficient.

The invention therefore extends generally to any embodiment falling within the scope of the appended claims, as seen in the light of the foregoing description and drawings.

The invention claimed is:

1. A method for performing X-ray analysis using a device (1) comprising an X-ray tube (2) and at least one capillary lens (4) for focusing the X-rays in a micro-region at a location (5) for a sample for analysis, in addition to a detector (6) for detecting X-ray fluorescence from the sample, wherein the device further comprises at least one energy-dependent filter (3) placed in the optical path between the X-ray tube and the location (5), characterized in that the method comprises the steps of:

a) determining the desired maximum dimensions ($X_{max}$) for the micro-region;

b) determining the energy ($E_{max}$) of the X-rays associated with the desired maximum dimensions ($S_{max}$) for the micro-region;

c) selecting a filter (3) which is adapted to block in considerable measure X-rays with an energy which is equal to or lower than a predetermined energy value, wherein the energy value is chosen to be substantially equal to the energy ($E_{max}$) determined in step b), such that the dimensions of the micro-region ($S_{max}$) are substantially bounded within predetermined permissible values.

2. A method as claimed in claim 1, wherein step c) comprises the steps of:
1. selecting filter material that is suitable for blocking in considerable measure X-rays with an energy which is equal to or lower than the energy ($E_{max}$) determined in step b),
2. determining the transmission characteristic (curve B) in a number of filters with differing thickness of the selected filter material; and
3. selecting a thickness for the filter material associated with a predetermined value for the permissible transmission of X-rays with an energy equal to the energy ($E_{max}$) determined in step b).

3. A method as claimed in claim 1, wherein the thickness of the filter (3) is smaller than or equal to 300 micrometers.

4. A method as claimed in claim 1, wherein the filter (3) comprises aluminum.

5. A method as claimed in claim 1, wherein the filter (3) is placed in the optical path between the X-ray tube (2) and the capillary lens (4).

6. A method as claimed in claim 1, wherein the X-ray tube (2) is a microfocus tube.

7. A method as claimed in claim 1, wherein the capillary lens (4) is a polycapillary lens.

\* \* \* \* \*